United States Patent
Yokota et al.

(10) Patent No.: US 12,002,376 B2
(45) Date of Patent: Jun. 4, 2024

(54) TRAINING APPARATUS, CATHETER, IMAGE PROCESSING METHOD, PROGRAM, AND INFORMATION RECORDING MEDIUM

(71) Applicants: RIKEN, Saitama (JP); UNIVERSITY OF THE RYUKYUS, Okinawa (JP)

(72) Inventors: Hideo Yokota, Saitama (JP); Yusuke Ohya, Okinawa (JP); Masashi Iwabuchi, Okinawa (JP)

(73) Assignees: RIKEN, Saitama (JP); UNIVERSITY OF THE RYUKYUS, Okinawa (JP)

( * ) Notice: Subject to any disclaimer, the term of this patent is extended or adjusted under 35 U.S.C. 154(b) by 766 days.

(21) Appl. No.: 17/046,571

(22) PCT Filed: Apr. 12, 2019

(86) PCT No.: PCT/JP2019/016037
§ 371 (c)(1),
(2) Date: Oct. 9, 2020

(87) PCT Pub. No.: WO2019/198826
PCT Pub. Date: Oct. 17, 2019

(65) Prior Publication Data
US 2021/0134185 A1    May 6, 2021

(30) Foreign Application Priority Data
Apr. 13, 2018   (JP) ................. 2018-077822

(51) Int. Cl.
*G09B 23/28*      (2006.01)
*G03B 11/00*      (2021.01)
(Continued)

(52) U.S. Cl.
CPC ............ *G09B 23/286* (2013.01); *G03B 11/00* (2013.01); *G03B 15/03* (2013.01); *G06T 7/0012* (2013.01);
(Continued)

(58) Field of Classification Search
CPC ..... G09B 23/28; G09B 23/285; G09B 23/286; G09B 23/30
See application file for complete search history.

(56) References Cited

U.S. PATENT DOCUMENTS 3,566,874 A * 3/1971 Shepherd .......... A61M 25/0009
424/422
4,058,910 A * 11/1977 Funk .................... G09B 23/30
40/381
(Continued)

FOREIGN PATENT DOCUMENTS

CN         1628602 A      6/2005
CN       202376554 U      8/2012
(Continued)

OTHER PUBLICATIONS

EP search Report in connection to EP Application No. 19784597.7, dated Dec. 2, 2021.
(Continued)

*Primary Examiner* — Peter R Egloff
(74) *Attorney, Agent, or Firm* — Meunier Carlin & Curfman LLC

(57) ABSTRACT

Provided is a system that enables training for catheter surgery without using radiation. The system offering training for catheter surgery includes: a light source; a blood vessel model to which a catheter having a fluorescent agent applied thereto is inserted; a tank in which the blood vessel model is placed; a filter for rejecting white light that is not transmitted through the blood vessel model, of illuminating light from the light source; a camera for imaging fluorescence transmitted through the filter; a driver for changing the attitude of the light source; and a computer that performs a process of reversing black and white of an image signal output from the camera.

17 Claims, 8 Drawing Sheets

(51) Int. Cl.
  *G03B 15/03* (2021.01)
  *G06T 7/00* (2017.01)
  *H04N 7/18* (2006.01)
  *H04N 23/56* (2023.01)
  *A61M 25/01* (2006.01)

(52) U.S. Cl.
  CPC ............. *H04N 7/183* (2013.01); *H04N 23/56* (2023.01); *A61M 2025/0166* (2013.01); *G03B 2215/0557* (2013.01); *G03B 2215/0589* (2013.01); *G06T 2207/10064* (2013.01); *G06T 2207/30021* (2013.01)

(56) References Cited

U.S. PATENT DOCUMENTS

| | | |
|---|---|---|
| 2005/0165303 A1 | 7/2005 | Kleen et al. |
| 2006/0062732 A1 | 3/2006 | Uchida et al. |
| 2011/0046476 A1* | 2/2011 | Cinquin ............... G09B 23/285 |
| | | 600/424 |
| 2011/0212426 A1 | 9/2011 | Gloeggler et al. |
| 2015/0196202 A1 | 7/2015 | Mercader et al. |
| 2016/0155363 A1* | 6/2016 | Rios ..................... G09B 5/00 |
| | | 434/262 |
| 2017/0143236 A1 | 5/2017 | Shekhar et al. |
| 2019/0103040 A1* | 4/2019 | Kerins ................ G09B 23/286 |
| 2019/0144594 A1* | 5/2019 | Maegawa ............. C08G 18/64 |
| | | 252/500 |

FOREIGN PATENT DOCUMENTS

| | | |
|---|---|---|
| CN | 106028914 A | 10/2016 |
| EP | 2772897 A1 | 9/2014 |
| JP | 2006-081619 A | 3/2006 |
| JP | 2012-071007 A | 4/2012 |
| JP | 201273490 A | 4/2012 |
| JP | 2014155510 A | 8/2014 |
| JP | 2014170075 A | 9/2014 |
| WO | 2002070980 A1 | 9/2002 |
| WO | WO-2018123300 A1 * | 7/2018 ............. A61L 29/06 |

OTHER PUBLICATIONS

Office Action in connection to CN application No. 20198002550.X, dated Oct. 21, 2021.
European Office Action in connection to EP Application No. 19784597.7, dated Aug. 11, 2023.

* cited by examiner (B)

(C)

TRAINING APPARATUS, CATHETER, IMAGE PROCESSING METHOD, PROGRAM, AND INFORMATION RECORDING MEDIUM

TECHNICAL FIELD

The present disclosure relates to training for intravascular treatment, and more specifically relates to a technique for offering training without using radiation.

BACKGROUND ART

Surgery using catheters is performed with x-ray radiation. Training for such surgery is also performed with an x-ray transmission apparatus. For example, Japanese Patent Laying-Open No. 2014-170075 (PTL 1) discloses "a training apparatus that easily establishes an environment in which liquid circulates and enables training based on x-ray imaging to be conducted, to thereby enable training close to more realistic interventional manipulation to be conducted efficiently and satisfactorily" (PTL 1).

CITATION LIST

Patent Literature

PTL 1: Japanese Patent Laying-Open No. 2014-170075

SUMMARY OF INVENTION

Technical Problem

Training conducted with x-ray radiation involves a problem that a physician undergoing the training is exposed to the radiation. Thus, there is a need for a technique that enables training for surgery without x-ray imaging.

The inventors have devised a method that uses fluorescence imaging as a training method for surgery using catheters. In the case of x-ray imaging, there is no significant difference between the x-ray absorption coefficient of a contrast agent for the x-ray imaging and the x-ray absorption coefficient of a guide wire (may also be referred to simply as "wire" hereinafter). Therefore, the guide wire is imaged as a shadow together with the contrast agent, and thus cannot be identified in a camera image, which is significant for the training for catheters. In contrast, in the case of fluorescence imaging, there is a difference between the absorption coefficient of a fluorescent contrast agent and that of the guide wire, and thus the catheter is clearly imaged. As such, it may possibly be difficult to enhance the training effect. Thus, there is a need for a technique that enhances the training effect of the catheter training without exposure to x-ray.

The present disclosure is given to solve the problems as described above, and an object in an aspect is to provide a technique that enhances the training effect without exposure to x-ray.

Solution to Problem

According to an embodiment, a training apparatus is provided. The training apparatus includes: a light source that illuminates an organ model in which a catheter is to be inserted, a fluorescent agent being applied to the catheter; a filter that rejects illuminating light from the light source and transmits fluorescence from the catheter; a camera that images transmitted light from the filter; a monitor that displays an image based on the transmitted light; and a computer that performs image processing using data that is output from the camera. The computer performs image processing for the catheter to be recognized, based on an amount of fluorescence from the catheter, and causes the catheter to be displayed or not to be displayed, based on data having undergone the image processing.

In an aspect, the light source is located on a side where the camera is disposed, with respect to the organ model. In this configuration, the camera images light reflected from the organ model. In this case, when a contrast agent for the organ model contains a fluorescent agent, the catheter is not imaged in spite of the fluorescent agent applied to the catheter, which may enhance the effect of training for catheter insertion.

In an aspect, the light source is located on a side opposite to a side where the camera is disposed, with respect to the organ model. In this configuration, the camera can image transmitted light from the organ model. For example, when a member like a guide wire that does not transmit light is inserted in the organ model, the member is imaged merely as a shadow. Thus, image processing can be performed to also cause the catheter not to be displayed, which can offer an opportunity of training appropriate for an intended purpose.

In an aspect, the training apparatus further includes a guide wire to be inserted in the catheter. The guide wire has its surface to which a fluorescent agent is applied. Such a configuration can offer training for manipulating the guide wire.

In an aspect, the training apparatus further includes, in addition to the above-described features, a computer that performs image processing using data that is output from the camera. From the data, the computer generates data for displaying a monochrome image. Based on the generated data, a monitor displays the monochrome image.

In an aspect, the training apparatus further includes a regulator that changes a direction of illumination of light from the light source toward the catheter. The direction of illumination can be changed, which facilitates estimation of where the blood vessel model branches, for example.

According to another embodiment, a catheter is provided. A fluorescent agent is applied to a surface of the catheter, and a hydrophilic coating is applied to a surface of a film of the fluorescent agent.

According to a further embodiment, an image processing method is provided. The image processing method includes: illuminating, with a light source, an organ model in which a catheter is inserted, a fluorescent agent being applied to the catheter; rejecting illuminating light from the light source and transmitting fluorescence from the catheter; performing image processing for the catheter to be recognized, based on an amount of fluorescence from the catheter, the amount of fluorescence being obtained by imaging transmitted light from the organ model in which the catheter is inserted, through a filter that transmits fluorescence; and causing the catheter to be displayed or not to be displayed, based on data having undergone the image processing.

According to a still further embodiment, a program for causing a computer to perform an image processing method is provided. The program causes the computer to execute: illuminating, with a light source, an organ model in which a catheter is inserted, a fluorescent agent being applied to the catheter; rejecting illuminating light from the light source and transmitting fluorescence from the catheter; performing image processing for the catheter to be recognized, based on an amount of fluorescence from the catheter, the amount of fluorescence being obtained by imaging transmitted light from the organ model in which the catheter is inserted, through a filter that transmits fluorescence; and causing the catheter to be displayed or not to be displayed, based on data having undergone the image processing.

According to a still further embodiment, there is provided a computer-readable information recording medium on which the above-described program is stored.

Advantageous Effects of Invention

In an aspect, training for insertion into an organ model can be conducted with a catheter and/or a guide wire to which a fluorescent agent is applied, without using x-ray imaging, and accordingly, exposure to radiation can be avoided.

The foregoing and other objects, features, aspects, and advantages of the present invention will be apparent from the following detailed description of the invention that will be appreciated in connection with the attached drawings.

DESCRIPTION OF EMBODIMENTS

Figure 1:
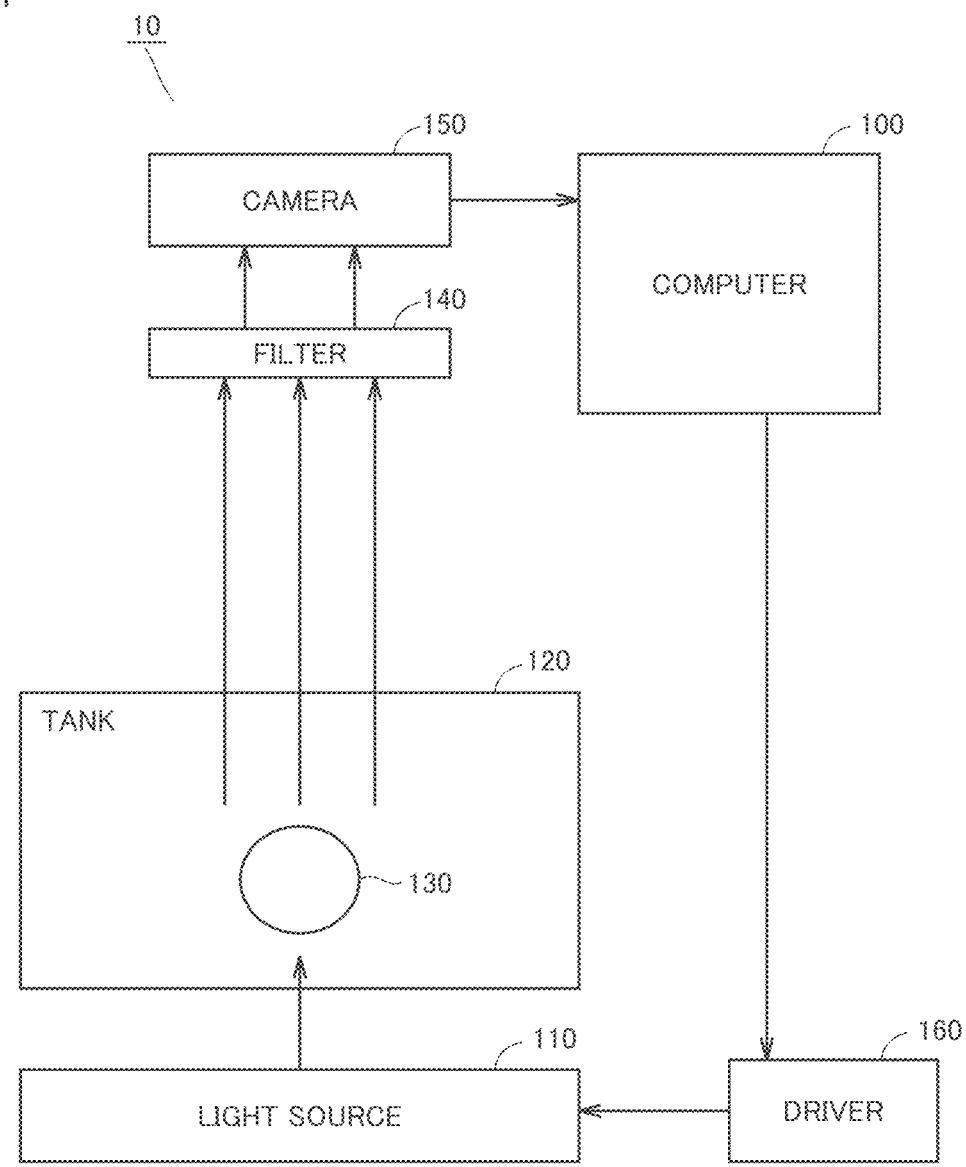
FIG. 1 shows a configuration of a training system according to one embodiment.

Embodiments of the present invention are described hereinafter with reference to the drawings. In the following description, the same components are denoted by the same reference characters. They are named identically and function identically. Therefore, a detailed description of them is not repeated herein.

[Technical Idea]

Initially, a technical idea for the present embodiment is described. In the present embodiment, fluorescence imaging of an organ model of a blood vessel is performed so as to provide an opportunity for training for insertion, into the organ model, of a catheter, a guide wire, and other elongated members. The elongated member may either be hollow (like a straw) or solid. In an aspect, a guide wire with a fluorescent contrast agent applied thereto is inserted in the organ model. Further, a catheter with a fluorescent agent applied thereto may be inserted along the guide wire. For example, along a guide wire to which a fluorescent contrast agent of a relatively lower concentration is applied, a catheter is inserted in an organ model, which is imaged with a fluorescent contrast agent of a relatively higher concentration. The fluorescent contrast agent is desirably water-soluble. A computer to which imaging data is input reverses, in real time, black and white of an image generated by a fluorescence camera, and processes the image so as not to allow a portion of a fluorescence brightness value corresponding to the guide wire (a brightness value lower than or equal to a certain value) to be displayed (masking). The catheter in the present embodiment is a catheter for training for intravascular treatment. Blood vessels to be subjected to intravascular treatment include blood vessels of the heart, the kidney, the liver, the brain, the feet, and the like.

[System Configuration]

Referring to FIG. 1, a system 10 according to an embodiment is described. FIG. 1 shows a configuration of system 10 according to one embodiment. System 10 includes a computer 100, a light source 110, a tank 120, a filter 140, a camera 150, and a driver 160. In tank 120, a blood vessel model 130 is placed as an example of the organ model. The attitude of light source 110 (the direction of illumination, for example) can be changed by driver 160. Driver 160 is controlled through manipulation of computer 100 or a control panel (not shown) to control the attitude of light source 110.

In an aspect, light source 110 is an excitation light source and may be configured as an LED (Light Emitting Diode) array. Light emitted from light source 110 illuminates tank 120. Light transmitted through tank 120 is transmitted through filter 140. In an aspect, filter 140 may be configured as an excitation light filter. Desirably, filter 140 is capable of at least rejecting the light emitted from light source 110. The light from filter 140 is imaged by camera 150. An image signal from camera 150 is input to computer 100.

In an aspect, blood vessel model 130 is made of a material transmitting excitation light and fluorescence, and may either be transparent or semitransparent. In another aspect, blood vessel model 130 may either be colored or colorless. For system 10, a fluorescent substance receiving light of a specific wavelength and emitting light of another wavelength may be used. System 10 may apply only the light of an excitation wavelength and detect only the fluorescence wavelength to detect a signal of a high S/N ratio. For fluorescence observation, only the object to be observed can be made bright and subjected to observation, to thereby enhance the detectability. When blood vessel models 130 imitating a plurality of blood vessels are placed in tank 120, different fluorescent pigments may be used for respective catheters, so that each catheter can be detected with high sensitivity.

In an aspect, sodium fluorescein ($C_{20}H_{10}Na_2O_5$), fluorescein isothiocyanate (FITC), or the like, for example, may be used as the fluorescent pigment. Light source 110 emits light having a wavelength of 488 nm that is the wavelength of a common excitation light source. Filter 140 transmits only the light having a wavelength of 510 nm, for example.

Figure 2:
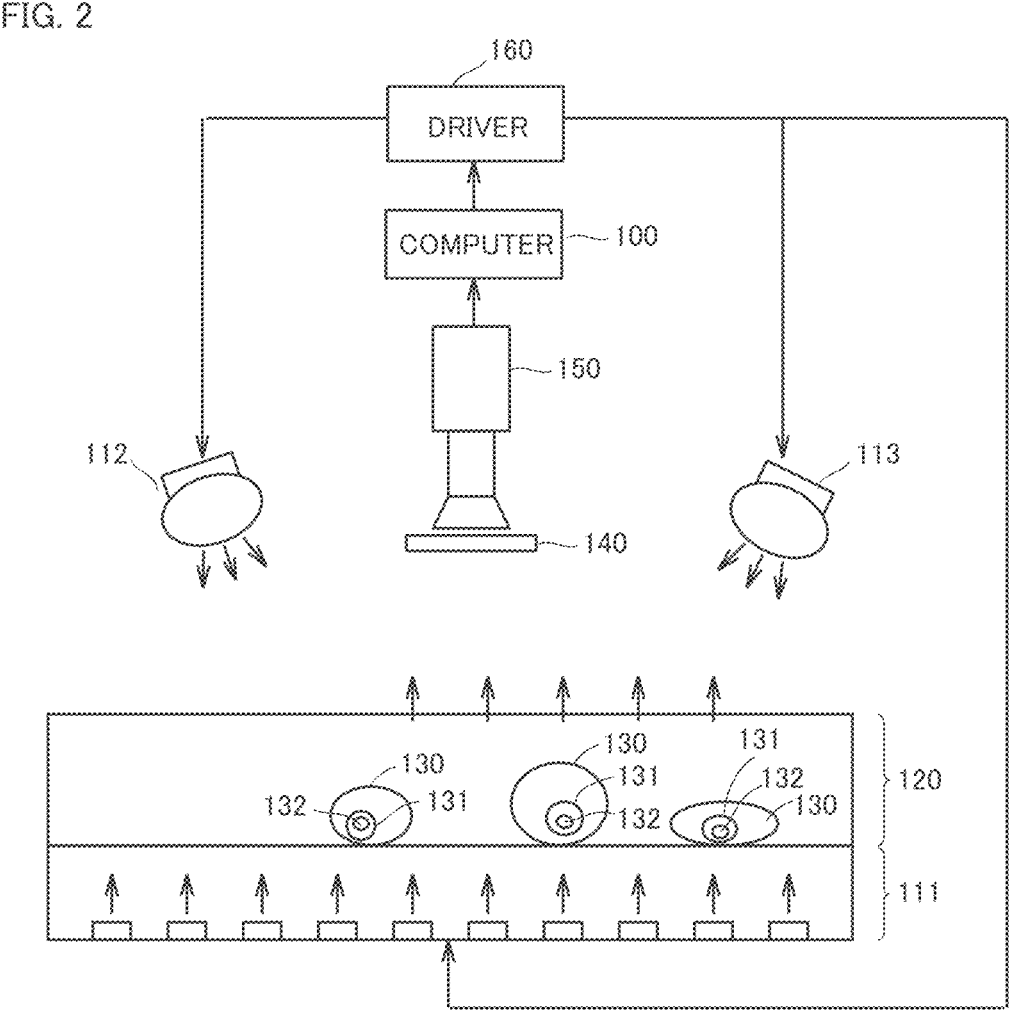
FIG. 2 shows a manner of illumination in a training system.

Referring to FIG. 2, a specific configuration of system 10 is described. System 10 includes excitation light sources 111, 112, 113, tank 120, filter 140, and camera 150. Excitation light source 111 is an LED array. Excitation light sources 112, 113 may be provided as extra light sources for the sake of fail-safe. In tank 120, a plurality of blood vessel models 130 are placed. In an aspect, the refractive index of a solution that fills tank 120 is substantially identical to the refractive index of blood vessel models 130. Accordingly, blood vessel models 130 in the solution have high transparency.

Each blood vessel model 130 is configured to allow a wire 132, a catheter 131, and/or other members to be inserted in the blood vessel model. A fluorescent dye is applied to a surface of catheter 131. Further, a hydrophilic coating is applied to a surface of the fluorescent dye. In an aspect, catheter 131 is made of a material transmitting excitation light and fluorescence, and may either be transparent or semitransparent. In another aspect, catheter 131 may be colored. Catheter 131 may be inserted in blood vessel model 130 along wire 132. A fluorescent dye is also applied to wire 132. Desirably, the brightness of the fluorescent dye applied to the surface of catheter 131 is at least higher than the brightness of the fluorescent dye applied to the surface of the wire. The brightness of the fluorescent dye may be different for each wire. The brightness includes the brightness for hiding the wire for the purpose of training, and the brightness for making the wire conspicuous. The training includes training for blood vessel model 130 before a contrast agent is injected in the model, and training for blood vessel model 130 after a contrast agent is injected in the model. The brightness of the fluorescent dye applied to the wire may be determined depending on the concentration of the contrast agent.

In an aspect, for the training using system 10, blood vessel model 130 in which catheter 131 has not been inserted is imaged prior to the start of the training. An image obtained through this imaging is used as a so-called mask image. Subsequently, upon the start of the training, a guide wire to which a fluorescent agent is applied is inserted in blood vessel model 130 and, in this state, excitation light source 111 or excitation light sources 112, 113 emit light. The excitation light source(s) to be caused to emit light varies depending on the purpose of the training. For example, if the training is conducted for which it is desirable not to image a flow path (blood vessel) of a contrast agent, desirably the brightness of the image of blood vessel models 130 is substantially identical to the brightness of the region of the solution. In this case, a controller of system 10 may control each of excitation light sources 112, 113 to illuminate blood vessel models 130 and the solution so that the brightness of reflected light is uniform. The conditions for imaging at this time are stored in system 10. Camera 150 images the reflected light, and then an imaging signal is input to computer 100.

Subsequently, a contrast agent is injected, and system 10 uses the stored imaging conditions to cause excitation light sources 112, 113 to illuminate blood vessel models 130 and the solution. Camera 150 images the light reflected from the illuminated blood vessel models and solution, and resultant imaging signals are input to computer 100. Computer 100 may calculate the difference between these imaging signals.

In another aspect, receiving a signal input from camera 150, computer 100 performs a process for reversing black and white of an image generated through the imaging. Further, computer 100 causes a portion of a fluorescence brightness value corresponding to catheter 131 (a brightness value less than or equal to a certain value) not to be displayed (masking). In this way, catheter 131 can be made hardly visible. The brightness of the black and white of an image obtained through x-ray imaging can be reversed appropriately. Therefore, for the fluorescence observation according to the present embodiment, the brightness of black and white of an image may be reversed like the x-ray imaging, as required.

In an aspect, when light is emitted from excitation light source 111 located opposite to camera 150 with respect to blood vessel model 130 and camera 150 images a catheter inserted in blood vessel model 130, the part of the external surface of catheter 131 that faces the camera 150 oriented in its imaging direction is not substantially illuminated with the light from excitation light source 111. Therefore, even when a fluorescent agent is applied to the external surface of catheter 131, fluorescence is not observed on the side where camera 150 is located and catheter 131 may be imaged as a shadow. In another aspect, when light is emitted from excitation light sources 112, 113 located on the same side as camera 150, fluorescence is emitted from the fluorescent agent applied to the external surface of catheter 131 and camera 150 can image catheter 131 as it is. Because the result of imaging thus varies depending on how catheter 131 is illuminated, the direction of illumination can be changed by making a switch between excitation light source 111 and excitation light sources 112, 113 depending on the intended purpose.

For example, for an actual surgical operation using catheters, there is an image obtained through visualization prior to injection of a contrast agent and an image obtained through visualization after injection of the contrast agent, and these images are seen differently. Similarly, it is desirable for an aspect of training that image data obtained by camera 150 is different depending on the purpose of the training.

In an aspect, camera 150 images, through a filter that transmits fluorescence, light transmitted through an organ model (blood vessel model 130, for example) in which inserted catheter 131 to which a fluorescent agent is applied and in which a guide wire (wire 132, for example) is inserted. A CPU of computer 100 reverses black and white of image data obtained through the imaging. The CPU performs a process of changing a color of a brightness value of an image of the guide wire to a color of a surrounding of the guide wire, and causes a monitor to display an image based on data having undergone the process.

In an aspect, a program for causing a computer to perform an image processing method causes computer 100 to perform the steps of: causing camera 150 to image, through a filter that transmits fluorescence, light transmitted through an organ model in which inserted a catheter to which a fluorescent agent is applied and in which a guide wire is inserted, and receiving input of a signal generated by the imaging; reversing black and white of image data obtained through the imaging; performing a process of changing a color of a brightness value of an image of the guide wire to a color of a surrounding of the guide wire; and causing a monitor to display an image based on data having undergone the process.

Differences generated depending on the position of the excitation light source(s) are described in conjunction with a guide wire. In an aspect, when the lumen in a transparent blood vessel is observed through fluorescence imaging, both excitation light sources 110, 111 and excitation light sources 112, 113 produce the same effects. Specifically, both the transparent lighting like excitation light sources 110, 111 and the reflective lighting like excitation light sources 112, 113 produce similar effects when the lumen in a transparent blood vessel is observed through fluorescence imaging, for example.

In another aspect, when a guide wire (to which no fluorescent agent is applied) is inserted in a model to be subjected to the above-described observation and the transparent lighting like excitation light sources 110, 111 is used, the guide wire which does not emit fluorescence is imaged as a shadow. In contrast, when the reflective lighting like excitation light sources 112, 113 is used and a fluorescent contrast agent is located between the guide wire and camera 150, the guide wire is invisible due to the presence of the fluorescent pigment and is not imaged by camera 150. In this case, depending on the angle of the direction of illumination by the reflective lighting like excitation light sources 112, 113, the form of the shadow of the guide wire may vary.

When the reflective lighting like excitation light sources 112, 113 is used, a fluorescent pigment applied to the guide wire emits fluorescence. In contrast, when the transparent lighting like excitation light sources 110, 112 is used, the part of the circumferential surface of the guide wire that is located on the same side as the camera is not exposed to excitation light, and thus the fluorescent pigment does not necessarily emit light. In view of this, depending on the visibility of the guide wire, desirably the amount of light or the angle of illumination of excitation light sources 110, 111 or excitation light sources 112, 113 is controlled.

Under the reflective lighting, the amount of light emission from a fluorescent substance applied to the guide wire remains substantially the same even when conditions are changed. Then, this characteristic can be utilized to perform image processing (such as threshold processing) based on the brightness information to enable identification of a site where the guide wire is located. After the site is identified, its color can be changed to the same amount of light as the surrounding fluorescence, so that the part is not shown in the resultant image. Moreover, the part may be displayed to a slight extent or the part may be displayed with emphasis. On the contrary, when the transparent lighting is used, a part of the guide wire that does not emit light may be identified and the guide wire may be displayed in the color of its surrounding, so as not to show the part, or emphasize the part.

The above can be implemented through image processing by a computer, and therefore, display can be implemented in various manners for training for insertion of a guide wire, for example. Moreover, it is unnecessary to make the amount of light from the fluorescent contrast agent identical to the amount of fluorescence from the guide wire, and therefore, the conditions for training can be determined easily and can be simply displayed.

While the foregoing description illustrates an example of the guide wire, the same is not limited to the guide wire but is applicable as well to catheters and stents.

Figure 3:
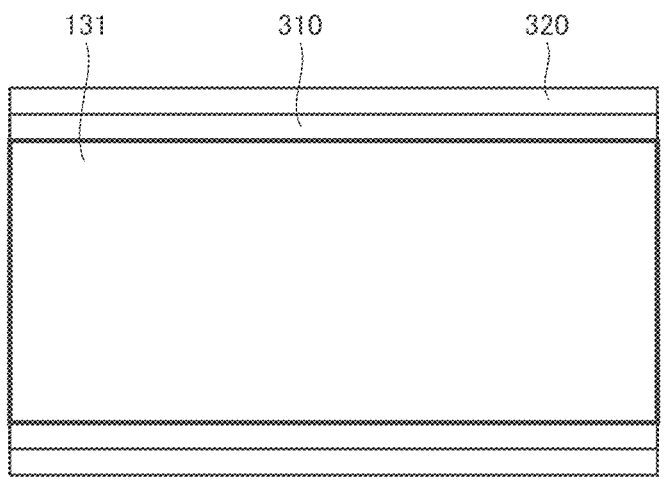
FIG. 3 shows a catheter with a fluorescent agent applied thereto.

Referring to FIG. 3, a structure of catheter 131 is described. FIG. 3 shows a cross-sectional structure of a catheter according to an aspect. A fluorescent dye 310 is applied to the external surface of catheter 131. A hydrophilic coating is applied to the surface of fluorescent dye 310. Catheter 131 having such a structure emits fluorescence, and therefore, a fluorescence portion can be imaged by rejecting, with a filter, white light of the light emitted from light source 110 and transmitted through tank 120. Then, black and white of an image obtained through the imaging may be reversed by a processor of a computer. Accordingly, the object (such as an image of the guide wire for example) that is desirably invisible to a trainee in terms of training is hardly visible, which may enhance the training effects.

In another aspect, when camera 150 images catheter 131 in which a guide wire is inserted, the guide wire is imaged black.

[Procedure of Operation]

Figure 4:
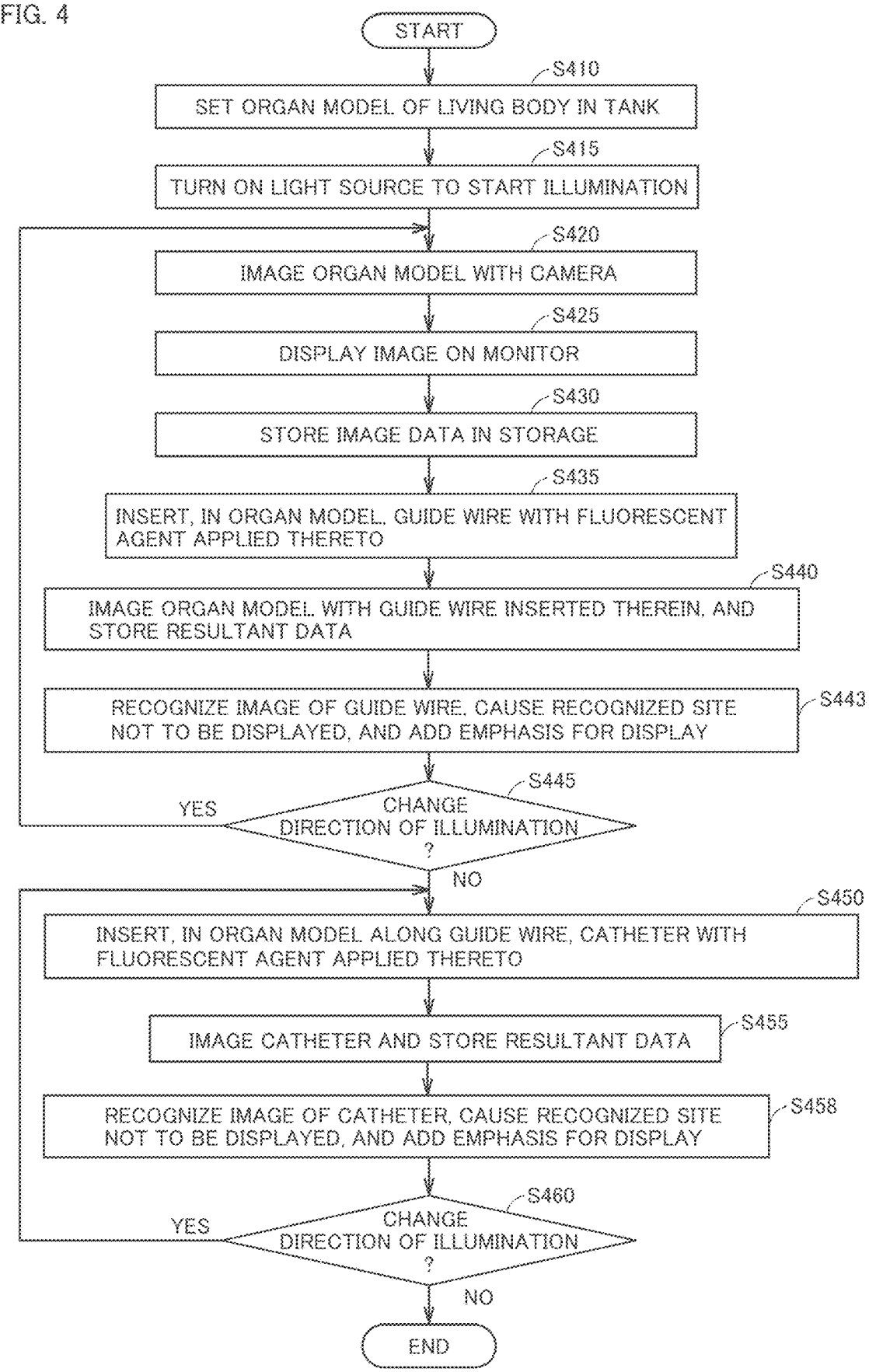
FIG. 4 is a flowchart showing a procedure of an operation performed by a training system.

Referring to FIG. 4, a procedure of an operation of system 10 according to an aspect is described.

In step S410, a user of system 10 sets an organ model (blood vessel model 130, for example) of a living body in tank 120, and places a solution in tank 120.

In step S415, the user turns on light source 110 to start illumination with light. The illuminating light emitted from light source 110 is transmitted through tank 120 and then transmitted through filter 140 to be incident on camera 150. A part of the illuminating light is applied to blood vessel model 130 to which fluorescent dye 310 is applied, and the remainder of the illuminating light is transmitted through the solution and incident on filter 140. As blood vessel model 130 is illuminated with the light from light source 110, blood vessel model 130 emits fluorescence. The fluorescence is incident on filter 140. Filter 140 rejects the wavelength of the illuminating light from light source 110 and transmits the fluorescence as it is. The light from filter 140 enters camera 150.

In step S420, camera 150 images the organ model (blood vessel model 130). In an aspect, camera 150 images a state where the light emitted from excitation light source 111 is transmitted through tank 120. In another aspect, camera 150 may image a state where the light emitted from excitation light sources 112, 113 is reflected from blood vessel model 130 and tank 120. Image signals obtained through this imaging are input to computer 100. For each image signal, computer 100 performs processing such as binarization and noise removal, and further performs image processing such as black and white reversal.

In step S425, computer 100 causes a monitor 8 to display an image obtained through the image processing as described above.

In step S430, computer 100 stores data of the image in a storage.

In step S435, a trainee inserts, in the organ model (blood vessel model 130, for example), a guide wire to which a fluorescent agent is applied.

In step S440, computer 100 images the state where the guide wire is inserted in the organ model (blood vessel model 130), and stores its data in the storage. Computer 100 uses the data to perform the above-described image processing and, based on the resultant data, computer 100 may cause the monitor to display an image. The image may either be a monochrome image or a color image.

In step S443, computer 100 performs a process of recognizing the image of the guide wire, a process of causing the site of the recognized guide wire not to be displayed, and a process of emphasizing the other site. For example, computer 100 causes a portion corresponding to the guide wire (e.g. a region where the fluorescence brightness value is less than or equal to a certain value) not to be displayed.

In step S445, an instructor or the trainee determines whether to change the direction of illumination of light. For example, when another catheter is to be inserted in another blood vessel model of blood vessel models 130, the light from light source 110 has to illuminate the other blood vessel model depending on its site. In this case, for appropriate training to be conducted, it is desirable to place the other blood vessel model appropriately between light source 110 and camera 150, so that the illuminating light that is not transmitted through the blood vessel model is appropriately rejected by filter 140. When the instructor or trainee determines to change the direction of illumination of light (YES in step S445), the flow returns to step S420 and the steps or operations after imaging are carried out again. Otherwise (No in step S445), the next training is conducted from step S450.

In step S450, the trainee inserts catheter 131 with a fluorescent agent applied thereto in the organ model along the guide wire. The light emitted from light source 110 illuminates catheter 131 in which the guide wire is inserted, and the solution. The light transmitted through the solution is rejected by filter 140, and fluorescence emitted from catheter 131 is transmitted through filter 140 to enter camera 150.

In step S455, camera 150 images catheter 131 inserted in the organ model, and resultant imaging data is input to computer 100. Computer 100 stores the imaging data in the storage.

In step S458, computer 100 performs a process of recognizing the image of catheter 131, a process of causing the site of the recognized guide wire not to be displayed, and a process of emphasizing the other site. The concentration of the fluorescent contrast agent applied to the surface of catheter 131 is lower than the concentration of the fluorescent contrast agent applied to the surface of blood vessel model 130. Therefore, until the fluorescent contrast agent on the surface of blood vessel model 130 is dissolved in the solution, the light emitted from light source 110 appears to illuminate blood vessel model 130 and catheter 131 is hardly visible to the trainee.

In step S460, the instructor or trainee determines whether to change the direction of illumination of light. When the instructor or trainee determines to change the direction of illumination of light (YES in step S460), the trainee performs the operation of step S450 again. In another aspect, the trainee may return to step S420 to continue the training from insertion of another catheter 131. Otherwise (NO in step S460), the trainee ends the training.

Figure 5:
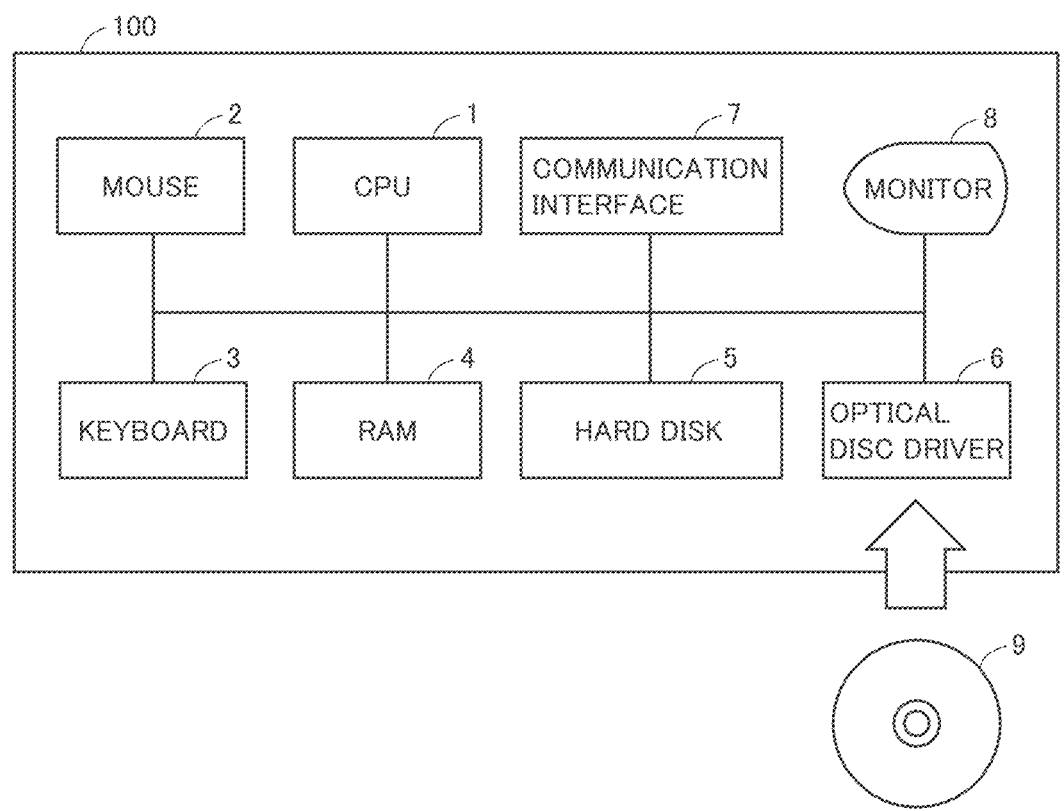
FIG. 5 is a block diagram showing a configuration of a computer.

Referring to FIG. 5, a configuration of computer 100 is described. FIG. 5 is a block diagram showing a hardware configuration of computer 100 according to an aspect.

Computer 100 includes, as main components, a CPU (Central Processing Unit) 1 executing a program having a plurality of instructions, a mouse 2 and a keyboard 3 that receive input of instructions from a user of computer 100, a RAM 4 that stores, in volatile manner, data generated through execution of the program by CPU 1, and data that is input through mouse 2 or keyboard 3, a hard disk 5 that stores data in nonvolatile manner, an optical disc driver 6, a monitor 8, and a communication interface 7. These components are connected to each other by a bus. An optical disc such as CD-ROM 9 or the like is mounted on optical disc driver 6. Communication interface 7 includes, but is not limited to USB (Universal Serial Bus) interface, wired LAN (Local Area Network), wireless LAN, Bluetooth® interface, and the like.

Processing by computer 100 is implemented by each hardware component and software executed by CPU 1. Such software may be stored in advance on hard disk 5. Alternatively, the software may be stored on CD-ROM 9 or another computer-readable nonvolatile data recording medium and distributed as a program product. Alternatively, the software may be provided as a downloadable program product by an information provider connected to the Internet or another network. Such software is read from the data recording medium by optical disc driver 6 or another data reader, or downloaded through communication interface 7, and thereafter stored on hard disk 5 temporarily. The software is read from hard disk 5 and stored in the form of an executable program on RAM 4 by CPU 1. CPU 1 executes the program.

The components forming computer 100 shown in FIG. 5 are common ones. The most essential element in the present embodiment may therefore be the program stored in computer 100. The operation of each hardware component of computer 100 is well known, and therefore, the detailed description thereof is not herein repeated.

The data recording medium is not limited to CD-ROM, FD (Flexible Disk), and hard disk, but may be a nonvolatile data recording medium that non-transitorily carries a program, such as magnetic tape, cassette tape, optical disc (MO (Magnetic Optical Disc)/MD (Mini Disc)/DVD (Digital Versatile Disc)), IC (Integrated Circuit) card (including memory card), optical card, and semiconductor memories such as mask ROM, EPROM (Electronically Programmable Read-Only Memory), EEPROM (Electronically Erasable Programmable Read-Only Memory), and flash ROM.

The program may herein include not only a program that is executable directly by CPU 1, but also a program in the form of a source program, a compressed program, an encrypted program, and the like.

In an aspect, system 10 according to the present embodiment include a C-shaped arm. On an upper part of the C-shaped arm, filter 140 and camera 150 are mounted. On a lower part of the C-shaped arm, light source 110 is mounted. Tank 120 may be disposed between light source 110 and filter 140. The C-shaped arm can be driven to change the position of incidence and the angle of incidence at which the illuminating light enters tank 120. The position of incidence and the angle of incidence of the illuminating light can be changed in various manners to estimate where the blood vessel model branches. Thus, with tank 120 fixed, training can be offered for insertion of a catheter into a blood vessel model that may be located at any of different positions.

Figure 6:
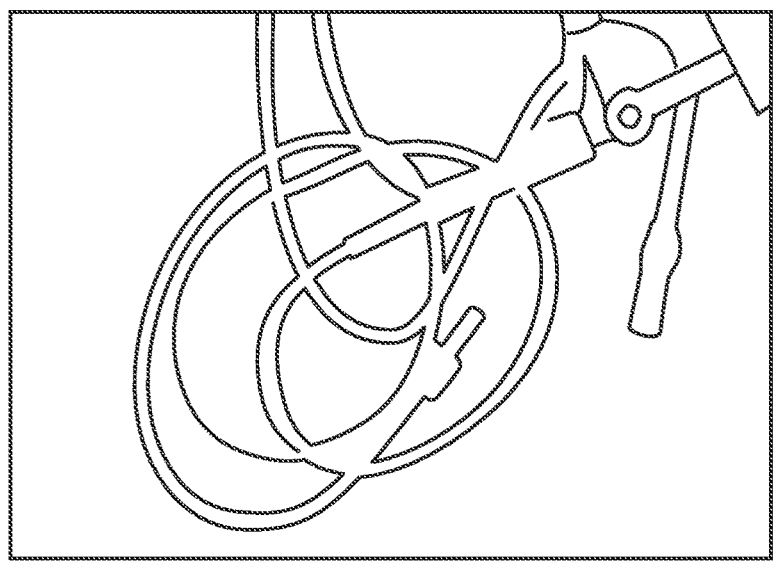
FIG. 6 shows images to which a technical idea according to the present disclosure is applied.
Figure 6:
Figure 6:
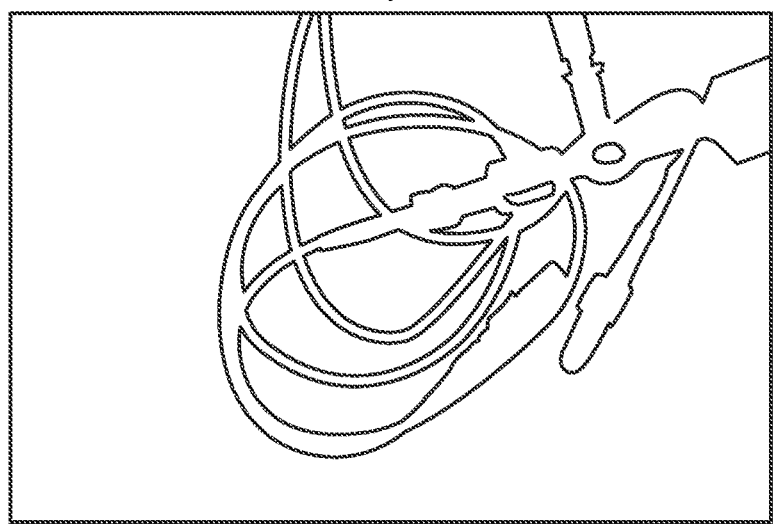
Figure 6:
Figure 6:
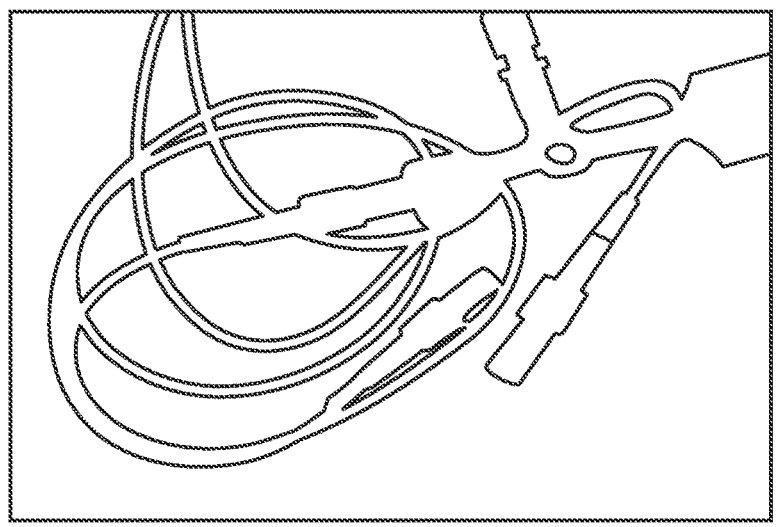

FIG. 6 shows images to which a technical idea according to the present disclosure is applied. FIG. 6 (A) is an image obtained by imaging an example of the organ model to which a fluorescent agent was applied and which was illuminated with white light. FIG. 6 (B) is an image obtained by imaging an example of the organ model to which a fluorescent agent was applied and which was illuminated with light at a wavelength of an excitation light source (488 nm for example). The aforementioned FITC was used as the fluorescent agent. A fluorescence filter transmits only the light having a wavelength of 510 nm, for example. A contrast agent injected in the inside of the organ model also contained a fluorescent agent. When a guide wire is inserted in the organ model and a catheter to which a fluorescent agent is applied is further inserted in the organ model, the guide wire is clearly imaged and the catheter is easily visible because of the difference in absorption coefficient between the guide wire and the contrast agent, which may nullify the training effect. Then, in order to make the catheter hardly visible, the image data obtained through imaging conducted after fluorescence is applied is subjected to a process of reversing black and white.

FIG. 6 (C) shows a state after the process of reversing black and white is performed on the image data shown in FIG. 6 (B). As the image shown in FIG. 6 (B) is generated and input to computer 100 in real time, CPU 1 performs the process of reversing black and white in real time, and further causes a fluorescence brightness value of the portion corresponding to the guide wire (brightness value less than or equal to a certain value) not to be displayed (masking). As a result, the guide wire becomes invisible and the position of the catheter cannot be identified, which can enhance the training effect.

Figure 7:
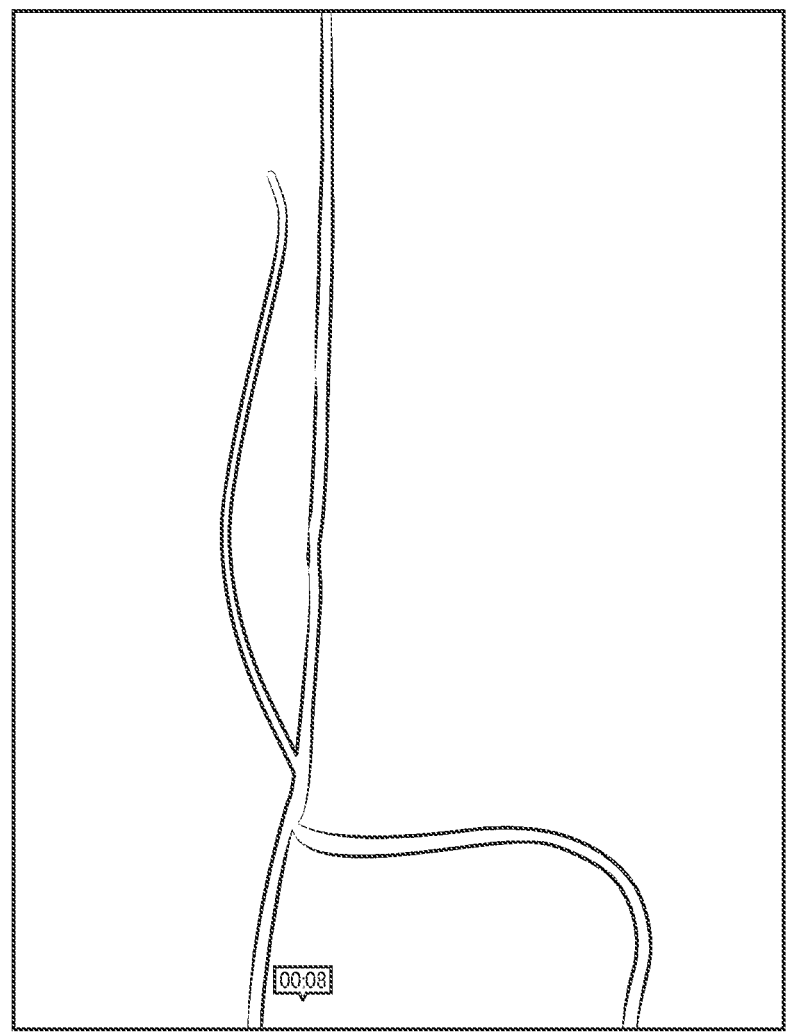
FIG. 7 shows a fluorescence image of an organ model with a guide wire inserted therein that is generated by illuminating the organ model by an excitation light source and imaging the organ model by a camera 150.
Figure 8:
FIG. 8 shows a black-and-white reversed image generated by a computer 100.

Referring to FIGS. 7 and 8, an image obtained according to one embodiment is described. FIG. 7 shows a fluorescence image of an organ model with a guide wire inserted therein that is generated by illuminating the organ model by an excitation light source and imaging the organ model by a camera 150. FIG. 8 shows a black-and-white reversed image generated by computer 100.

As shown in FIG. 7, when the organ model in which the guide wire is inserted is illuminated with an excitation light source, the guide wire is visible before a contrast agent is injected. When a contrast agent containing a fluorescent pigment is subsequently injected, the guide wire becomes invisible as shown in FIG. 8 due to the fluorescent pigment, and accordingly, training for insertion of the guide wire can be implemented.

In this way, the present embodiment enables training with a catheter without x-ray imaging, and can therefore prevent the trainee from being exposed to radiation.

It should be construed that embodiments disclosed herein are given by way of illustration in all respects, not by way of limitation. It is intended that the scope of the present invention is defined by claims, not by the description above, and encompasses all modifications and variations equivalent in meaning and scope to the claims.

REFERENCE SIGNS LIST 10 system; 100 computer; 110, 111, 112, 113 light source; 120 tank; 130 blood vessel model; 131 catheter; 140 filter; 150 camera; 160 driver; 310 fluorescent agent; 320 hydrophilic coating

The invention claimed is:

1. A training apparatus comprising:
  a light source that illuminates an organ model in which a catheter is inserted, a fluorescent agent being applied to the catheter;
  a filter that rejects illuminating light from the light source and transmits fluorescence from the catheter;
  a camera that images transmitted light from the filter;
  a monitor that displays an image based on the transmitted light; and
  a computer that performs image processing using data that is output from the camera,
  the computer
    performing image processing for the catheter to be recognized, based on an amount of fluorescence from the catheter, and
    causing the catheter to be displayed or not to be displayed, based on data having undergone the image processing.

2. The training apparatus according to claim 1, wherein the light source is located on a side where the camera is disposed, with respect to the organ model.

3. The training apparatus according to claim 1, wherein the light source is located on a side opposite to a side where the camera is disposed, with respect to the organ model.

4. The training apparatus according to claim 1, further comprising a regulator that changes a direction of illumination of light from the light source toward the catheter.

5. A catheter comprising:
  a fluorescent agent applied to a surface of the catheter; and
  a hydrophilic coating applied to a surface of a film of the fluorescent agent.

6. An image processing method comprising:
  illuminating, with a light source, an organ model in which a catheter is inserted, a fluorescent agent being applied to the catheter;
  rejecting illuminating light from the light source and transmitting fluorescence from the catheter;
  performing image processing for the catheter to be recognized, based on an amount of fluorescence from the catheter, the amount of fluorescence being obtained by imaging transmitted light from the organ model in which the catheter is inserted, through a filter that transmits fluorescence; and
  causing the catheter to be displayed or not to be displayed, based on data having undergone the image processing.

7. The training apparatus according to claim 1, wherein:
  a fluorescent agent is applied to a surface of the catheter; and
  a hydrophilic coating is applied to a surface of a film of the fluorescent agent.

8. The training apparatus according to claim 1, wherein:
  a fluorescent agent is applied to a surface of the catheter; and
  brightness of the fluorescent agent is larger than brightness of a fluorescent agent applied to a surface of a wire that guides the catheter.

9. The catheter according to claim 5, wherein:
  brightness of the fluorescent agent is larger than brightness of a fluorescent agent applied to a surface of a wire that guides the catheter.

10. The image processing method according to claim 6, wherein the light source is located on a side where the camera is disposed, with respect to the organ model.

11. The image processing method according to claim 6, wherein the light source is located on a side opposite to a side where the camera is disposed, with respect to the organ model.

12. The image processing method according to claim 6, further comprising:
  changing a direction of illumination of light from the light source toward the catheter.

13. The image processing method according to claim 6, wherein:
  a fluorescent agent is applied to a surface of the catheter; and
  brightness of the fluorescent agent is larger than brightness of a fluorescent agent applied to a surface of a wire that guides the catheter.

14. The image processing method according to claim 6, wherein:
  brightness of the fluorescent agent is larger than brightness of a fluorescent agent applied to a surface of a wire that guides the catheter.

15. The training apparatus according to claim 1, wherein a surface of the catheter is transparent.

16. The catheter according to claim 5, wherein a surface of the catheter is transparent.

17. The image processing method according to claim 6, wherein a surface of the catheter is transparent.

* * * * *